United States Patent
de Oliveira Barbosa Nachbaur et al.

(10) Patent No.: US 11,707,473 B2
(45) Date of Patent: Jul. 25, 2023

(54) METHOD FOR THE MANUFACTURE AND USE OF A BIONIC HYDROGEL COMPOSITION FOR MEDICAL APPLICATIONS

(71) Applicant: Qventis GmbH, Henningsdorf (DE)

(72) Inventors: Lidia de Oliveira Barbosa Nachbaur, Berlin (DE); Giuseppe Alonci, Hohen Neuendorf (DE)

(73) Assignee: Qventis GmbH, Henningsdorf (DE)

( * ) Notice: Subject to any disclaimer, the term of this patent is extended or adjusted under 35 U.S.C. 154(b) by 234 days.

(21) Appl. No.: 16/710,301

(22) Filed: Dec. 11, 2019

(65) Prior Publication Data

US 2020/0179419 A1    Jun. 11, 2020

(30) Foreign Application Priority Data

Dec. 11, 2018  (LU) .................................. LU101045

(51) Int. Cl.
*A61K 31/702*    (2006.01)
*A61K 47/69*    (2017.01)

(52) U.S. Cl.
CPC ........ *A61K 31/702* (2013.01); *A61K 47/6903* (2017.08)

(58) Field of Classification Search
CPC .. A61K 47/42; A61K 47/6903; A61K 31/738; A61K 31/702; A61K 8/735; A61K 8/442; A61K 9/0019; A61K 9/0014; A61K 9/06; A61K 9/0024; C08B 37/002; A61P 19/02; A61P 17/02
USPC .................................................... 514/54, 61
See application file for complete search history.

(56) References Cited

U.S. PATENT DOCUMENTS

| 2003/0096879 | A1* | 5/2003 | Fratini .................... A61K 47/36 516/98 |
| 2007/0196426 | A1 | 8/2007 | Hermitte et al. |
| 2009/0263447 | A1 | 10/2009 | Asius et al. |
| 2014/0142190 | A1 | 5/2014 | Piron et al. |
| 2016/0113855 | A1* | 4/2016 | Njikang ................ A61Q 19/00 514/54 |
| 2020/0017941 | A1 | 1/2020 | Matthey |

FOREIGN PATENT DOCUMENTS

| AU | 2017/276280 A1 | 1/2018 |
| WO | WO 2004/067575 A1 | 8/2004 |
| WO | 2010/131175 A1 | 11/2010 |
| WO | 2011/148116 A2 | 12/2011 |
| WO | 2012/068619 A1 | 5/2012 |
| WO | WO 2012/068619 A1 * | 5/2012 ............... A61K 6/64 |

OTHER PUBLICATIONS

Hoke, J. Clin. Invest., 2011, 121(11), 4231-4234.*
Shay, Clinical Infectious Diseaes, 2002, 34, 1215-1223.*
Tomihata K et al: "Crosslinking of Hyaluronic Acid With Water-Soluable Carbodiimide", Journal of Biomedical Materials Reasearch, Wiley, New York, NY, US, vol. 37, No. 2, Nov. 1, 1997, pp. 243-251.
Xing et al., Intra-articular Hyaluronic Acid in Treating Knee Osteoarthritis: a PRISMA—Compliant Systematic Review of Overlapping Meta-analys, Scientific Reports, 2016, 6, 32790.
Bellamy N, Campbell J, Welch V, Gee TL, Bourne R, Wells GA. Viscosupplementation for the treatment of osteoarthrtis of the knee. Cochrane Database of Systematic Reviews 2006, Issue 2. Art. No. CD005321.
Kornev et al., Hydrogel-assisted neuroregeneration approaches towards brain injury therapy: A state-of-the-art review, Computational and Structural Biotechnology Journal, 2018, 16, 488-502.
Özgegnel, Effects of hyaluronic acid on peripheral nerve scarring and regeneration in rats, Microsurgery, 2003, 23, 575-581.
Price et al., The role of hyaluronic acid in wound healing: assessment of clinical evidence, Am J Clin Dermatol, 2005, 6 (6), 393-402.
Al-Khateeb and Olszewska-Czyz, Biological molecules in dental applications: hyaluronic acid as a companion biomaterial for diverse dental applications, Heliyon, 2020, 6.
Alonci et al. (2021) "Physico-Chemical Characterization and In Vitro Biological Evaluation of a Bionic Hydrogel Based on Hyaluronic Acid and L-Lysine for Medical Applications" Pharmaceuticals 113:1194.
Extended European Search Report dated May 7, 2020 in corresponding European Patent Application No. 19215098.5.
Graca et al. (2020) "Hyaluronic acid—Based wound dressings: A review" Carbohydrate Polymers 241: 116364.
Kawano et al. (2021) "Wound Healing Promotion by Hyaluronic Acid: Effect of MolecularWeight on Gene Expression and In Vivo Wound Closure" Pharmaceuticals 14:301.
La Gatta et al. (2017) "Hyaluronan hydrogels with a low degree of modification as scaffolds for cartilage engineering" International Journal of Biological Macromolecules 103 pp. 978-989.
Murray et al. (2019) "Development and use of biomaterials as wound healing therapies" Burns & Trauma 7:2.
Ud-Din et al. (2014) "Regenerative healing, scar-free healing and scar formation across the species: current concepts and future perspectives" Experimental Dermatology 23: 615-619.

(Continued)

*Primary Examiner* — Ganapathy Krishnan
(74) *Attorney, Agent, or Firm* — Leydig, Voit & Mayer

(57) ABSTRACT

The invention relates to a method for the stabilization of a polysaccharide (hyaluronic acid) with a biomolecule—amino acid—through crosslinking, to generate a bionic hydrogel based on physiological building blocks for applications in regenerative medicine. The designed biosimilar hydrogel is intended to be used in regenerative medicine for the purpose of regenerate, rejuvenate and/or restore the structure or function of impaired or damaged tissues, and to promote healing. The manufacture method is composed of a single step that includes mixing L-lysine and hyaluronic acid sodium salt in an aqueous saline solution with either EDC/NHS as coupling agent.

11 Claims, 4 Drawing Sheets

(56) References Cited

OTHER PUBLICATIONS

Yang et al. (2021) "Role of Hyaluronic Acids and Potential as Regenerative Biomaterials in Wound Healing" ACS Appl. Bio Mater. 4(1): 311-324.

* cited by examiner

METHOD FOR THE MANUFACTURE AND USE OF A BIONIC HYDROGEL COMPOSITION FOR MEDICAL APPLICATIONS

BACKGROUND OF THE INVENTION

Field of the Invention

The field of the present invention relates to the manufacture and medical use of a bionic hydrogel composition.

Brief Description of the Related Art

New medical procedures with biosimilar biomaterials i.e. composed of biological/native ingredients are of outmost importance for use in regenerative medicine. The ultimate goal of regenerative medical treatments is to stimulate the body's own regeneration and healing ability.

The biocompatibility is very important for the process of regeneration, rejuvenation, replacement and repair of impaired structures or functions since it determines the body's acceptance and will minimize side effects. Biomaterials made exclusively of biological building blocks, such as carbohydrates and amino acids, under the condition of being free of residual by-products are chemically most suited for regenerative medicine.

As regards the design of regenerative medical solutions, it is of outmost importance to follow a bionic approach. Bionic design means integrating the information of structure, function and biological process into the design development of new medical solutions. The bionic design of a regenerative medical solution is the result of combining the information taken from biological systems together with the state of the art of science and knowledge to access feasibility, features and manufacturing route for develop a novel medical tool.

Hydrogels have already been widely employed in medical treatments for internal and external use. This kind of biomaterials are well tolerated by human tissues since they have a high degree of hydration. They may be non-resorbable or resorbable, whereas the latter ones have in general a higher biocompatibility profile. The resorption time may be tuned depending on the intended medical application.

One of the most requested cosmetic treatments involves the use of a dermal filler, such as hyaluronic acid, to give a younger appearance by replacing volume loss during the normal ageing. Hyaluronic acid is a polysaccharide naturally present in the human body. It is responsible for skin elasticity and it is a key player in physiological processes such as skin ageing, wrinkle formation, wound healing and scarring. For these reasons, hyaluronan-based formulations are widely used in skin care formulations and as intradermal injectables to reduce the severity of wrinkles and restore soft tissue volume. Pure hyaluronic acid is, however, quickly metabolized and degraded in the skin and thus frequent injections are required. Indeed, modern commercial formulation contains crosslinked hyaluronic acid—with the most commonly employed crosslinker being 1,4-butanediol diglycidyl ether (BDDE)—to ensure a long-lasting effect.

Hyaluronic acid is a non-sulfated glycosaminoglycan, composed of repeating disaccharide unit of D-glucuronic acid and N-acetyl-D-glucosamine. Glycosaminoglycans (GAGs) are negatively charged linear polysaccharides, normally sulfated (with hyaluronic acid being the only exception); they are present in all the animal and they are component of the cell membrane and the extracellular matrix, but they also act as shock absorbers and lubricants. The term hyaluronan (HA) is commonly employed to refer both to the protonate or deprotonated form. HA is a major component of the skin, extracellular matrix, cartilage, vitreous and synovial fluid.

The presence of carboxyl and OH groups gives HA strong hydrophilicity and is responsible for its high viscosity profile even at low concentrations. The molecular weight of HA depends from its origin and it is one of the most important differences between human and bacterial HA. Hyaluronic acid obtained from bacteria fermentation has shorter chains of ≈5000 disaccharide units (molecular weight of ~2-3 Mio. Dalton), while animal-derived HA has a molecular weight that can range from 4 to 6 Mio. Dalton. The chemical structure of HA is the same independent of the source or origin, thus allowing the use of bacteria-derived HA in humans without risk of immunologic response.

Interestingly, the molecular weight of HA can be different in different locations of the same organism, reflecting different functions: in animals, high molecular weight HA is usually present in healthy tissue, while low-molecular weight HA is involved in inflammation and angiogenesis. Hyaluronic acid connects cells with the extracellular matrix by binding with hyaladherins, a class of proteins that can be found on the ECM and on the cell surface. The most important among the HA receptors is the CD44 antigen, that by the formation or cleavage of connections with HA affects ECM remodeling. Hyaluronic acid aggregates are involved also in giving resistance to compression to cartilage.

Hyaluronic acid homeostasis is a dynamic process that involves competition between synthesis and degradation. HA is synthesized by hyaluronan synthases—integral membrane enzymes localized in the surface of the plasma membrane—and degraded both by the enzyme's hyaluronidases and by free-radical mechanisms not involving any enzymes. The half-life of HA is less than 10 minutes in the bloodstream, but it can be of several weeks in the cartilage.

Skin is a complex system regulated by the interactions of different layers of specialized cells with the external environment, skin annexes, the subcutaneous fat and the deep fascia is one of the main components of the integumentary system. It covers the whole surface of the body and its responsible of about 15% of the total adult weight. It and can be divided in three main layers: the epidermis (outer layer), the dermis and the hypodermis (or subcutis, the deepest layer).

Skin ageing is a complex natural process that involves drastic changes in the dermal layer with time and is associated with wrinkling and loss of skin tone and elasticity. It is possible to distinguish between two different ageing processes. Innate (or intrinsic) ageing is a physiological process involving all the organs of the body and is influenced, among the other factors, by the reduced production of sexual hormones. Extrinsic ageing is an effect of the influence of the external environment and it is caused by factors such as UV exposure, mechanical stress, pollution, smoking or exposure to chemical agents. From a molecular point of view, both extrinsic and intrinsic ageing lead to oxidative stress, cellular senescence and increase in the activity of matrix metalloproteases, that in the end result in a degradation of the collagen fibers, reduced collagen synthesis and reduced skin moisture, that lead to a significative decrease in soft tissue volume.

Another important marker for skin ageing is the reduction of hyaluronic acid in the epidermis, despite being still present in the dermis. In the epidermis, HA is normally synthesized in the basal stratum germinativum (where it is present intracellularly), and then it is excreted in the *spinosum* and granular layer where it is one of the components of the ECM. Here it plays a fundamental role in protecting the skin from dehydration. A study by E. Papakonstantinou and coworkers published in 2009 suggests that extrinsic ageing induced by photodamage may influence the balance between hyaluronan synthase and hyaluronidases and to a lower molecular HA in the epidermis.

Dermal fillers are widely employed to compensate the loss of soft tissue volume, reducing the amount and severity of wrinkles and folds. The first use of a facial filler was reported in 1983 by Dr. Franz Neuber, who used autologous upper arm fat to remodel facial defects caused by tuberculosis. In the following years, other researches started to use paraffine or silicon oil, that however were still prone to severe complications and were banned from FDA in 1970.

A big step forward was made in 1981 when FDA approved the use of a dermal filler based on bovine collagen (Zyderm), which however can trigger immunologic response.

The first hyaluronic acid-based dermal filler—Restylane—got approval for human use in 2003 and had an immediate success, because of its safety and no immunologic response is prompted from its injection. Today, a broad range of products are available on the market, from synthetic fillers based on calcium hydroxyapatite (Radiesse) to other polymer-based products (Sculptra and Artefill), with different cosmetic applications depending on the characteristic of the gel injected. Some of the most famous products available on the market based on hyaluronic acid are Restylane, Perlane, Juvederm, Juvederm Voluma and Belotero, that differ in the crosslinking methodology of hyaluronic acid, and further parameters e.g. swelling, molecular weight and the microscopic structure of the gel (monophasic or biphasic).

As stated before, pure hyaluronan is not suitable as a dermal filler, because of the fast turnover rate in the skin that would require multiple injections. A variety of crosslinking strategies are possible, which have a deep impact in the final properties of the gel. Crosslinking has two effects on hyaluronic acid:
 a. It reduces the resorption time, allowing each injection to last for several months;
 b. It changes the mechanical properties of hyaluronan and lead to a soft hydrogel instead of a viscous fluid.

Dermal fillers currently available in the market have generally an elastic modulus that ranges from 0.1 to 1 kPa, well below the elastic modulus of skin of 3 MPa. Rheological properties are of great importance both for the physician and for the patient. Harder gels, such as Restylane or Perlane (G'=600-700 Pa) can better resist the deformation induced by muscle movement but can also more easily induce pain and inflammation or be "felt" by the patient, while softer gels (Hylaform or Juvederm, G'=100-250 Pa) are generally indicated for superficial dermal injections.

The degree of crosslinking and the molecular structure of the crosslinker employed are the two most important differences among the products available in the market.

Hyaluronic acid crosslinking is generally performed in the cosmetic industry by reaction of the hydroxyl groups of HA with a crosslinker. The two most used crosslinking agents are divinylsulfone (DVS), employed by Prevelle Silk, Captique and Hylaform families of products, and butanediol diglycidyl ether (BDDE), that is used in Restylane, Perlane and Juvéderm fillers. Other possibilities are the use of biscarbodiimide (BCDI, Elevess) and of 1,2,7,8-diepoxyoctane (DEO, Puragen). However, a great number of other possibilities are under investigation, but they are not available in the medical aesthetic market, including direct modification of hyaluronic acid by acrylation and oxidation, crosslinking with adipic acid dihydrazide and coupling of other molecules through the carboxylic group on the glucuronic moiety.

Most of these new methods are not scalable to the industrial level due to the number of purification steps involved, the very high price of the molecules employed or the toxicity of initiators and other by products.

BDDE is the most used crosslinker in the hyaluronic acid industry. However, even if BDDE-crosslinked hyaluronic acid is considered to be safe—and this is true also for all the related byproducts of degradation after injection—BDDE by itself is toxic and it is of great importance to remove all the unreacted crosslinker from the final product. Toxicity can be a concern if we consider that a certain amount of BDDE can react only on one of the two extremities of the molecule, thus leaving a free reactive epoxy group.

Finding a substitute for BDDE would thus be beneficial, especially if it is replaced by a biomolecule such as a protein or an amino acid, for example L-Lysine.

L-Lysine is an amino acid physiologically present in the body and it plays an important role in cell adhesion and collagen cross-linking. For example, polylysine is used to enhance cell adhesion in tissue culture. The use of L-Lysine as a substitute crosslinker for BDDE would not only improve the biocompatibility of a HA hydrogel but it can also enhance cell adhesion and proliferation to hyaluronic acid.

Published U.S. Patent Application No. US 2016/0113855 A1 discloses fluid compositions comprising a matrix polymer and stabilizing component, methods of making such fluid compositions, and methods of treating skin conditions in an individual using such fluid compositions. The inventors employ the classic EDC/NHS chemistry (1-Ethyl-3-(3-dimethylaminopropyl)carbodiimide/N-hydroxysuccinimide) to activate the HA toward amines, however the method of this document is not suitable for the cross-linking of pure L-Lysine. Indeed, L-Lysine contains a carboxylic group that in the conditions used in US 2016/0113855 A1 would result in a less-stable ester bond. For this reason, the inventors report the use of lysine methyl ester during synthesis, followed by a second step of hydrolysis, that leads to the release of highly toxic methanol. The use of unprotected L-Lysine is reported in this document but appears not to be applicable under the reported conditions because the carboxylic group in the alfa carbon of the L-Lysine would be activated and react to form an ester bond with HA. Furthermore, the method disclosed in US 2016/0113855 A1 requires raising the pH up to 12 and performing the hydrolysis reaction at 50° C. for five minutes. This not only will lead to a degradation of the product due to the high pH and temperature, but also gives no certainty upon the completeness of the hydrolysis reaction. For clinical use, the presence on lysine methyl ester in the final product would be dangerous, because a chronic release of methanol can occur. Thus, US 2016/0113855 A1 does not teach a one-step method without the need of any subsequent hydrolysis step that can lead to the degradation of the material or the release of highly toxic molecules, such as methanol.

Published U.S. Patent Application No. 2009/0263447 A1 relates to crosslinked hyaluronic acid that can be obtained according to a process comprising: (a) activation of hyaluronic acid, (b) reaction of the activated hyaluronic acid with an oligopeptide- or polypeptide-based crosslinking agent, in a reaction medium adjusted to a pH of from 8 to 12, so as to obtain a crosslinked hyaluronic acid, (c) adjustment of the pH of the reaction medium to a value ranging from 5 to 7, and (d) precipitation of the crosslinked hyaluronic acid from an organic solvent. The document also relates to the above process, to a hydrogel obtained from the crosslinked hyaluronic acid and to the use of the crosslinked hyaluronic acid for the manufacture of implants that can be used in particular in plastic surgery. It is to be noted that this document relates to the use of di-lysine, which is much more expensive than standard L-lysine. The chemical reaction disclosed in US 2009/0263447 A1 is performed at a pH above 8.5, which is important in the EDC/NHS activation of the carboxylic groups of HA to obtain a good yield and a good reproducibility—that are mandatory for any industrial application and to avoid the formation of the ester bonds. Further, the cross-linking requires the presence of a significative amount of the co-reactant diisopropylethylamine (DIEA), that is added as 5-fold excess (in moles) in respect to EDC and more than 15 times excess in respect to dilysine. DIEA is a hazardous chemical and, according to the available safety data sheet, it is reported to be highly flammable and toxic if swallowed; it also causes severe skin burns and eye damage and it is harmful to aquatic life with long lasting effects.

The publication by Tomihata and Ikada (Journal of Biomedical Materials Research, Vol. 37, No. 2, 1997, p. 243-251) teaches a process for the manufacture of HA-films, that however is not applicable for the synthesis and/or industrial production of cross-linked HA hydrogels. The authors report a strategy for the crosslinking of HA with Lysine in presence of EDC. However, in their method they employ aqueous mixtures of organic solvents and EDC is used alone, without the co-reactant NHS. In the absence of a co-reactant, EDC can hydrolize quickly in water. Also, sell-esterification of HA is promoted, instead of the crosslinking with L-Lysine bridges. This would lead to a unstable gel that can quickly hydrolyze in water. This strategy cannot be applied industrially and is not effective, as confirmed by the fast degradation rate (15 days in rats).

In published International patent application No. WO 2012/068619 A1 provides therapeutic compositions and/or formulations which comprise at least one cross-linked protein matrix, wherein the at least one cross-linked protein matrix comprises at least one protein residue and at least one saccharide-containing residue, and methods of producing the same. The cross-linked protein matrix may be derived from cross-linking a full length or substantially full-length protein, such as tropoelastin, elastin, albumin, collagen, collagen monomers, immunoglobulins, insulin, and/or derivatives or combinations thereof, with a saccharide containing cross-linking agent, such as a polysaccharide crosslinking agent derived from, for example, hyaluronic acid or a cellulose derivative. This document relates to crosslinking a full-length protein to hyaluronic acid.

Published U.S. patent application no. US 2014/142190 A1 teaches that biodegradable single-phase cohesive hydrogels are useful, e.g., for the formulation of viscosupplementation compositions or compositions for filling wrinkles, contain a homogeneous blend of crosslinked polymers, which may be identical or different, crosslinked prior to the interpenetration thereof by mixing in the form of a single-phase hydrogel, wherein such crosslinked polymers are insoluble in water and miscible with one another, the hydrogels are such that the polymers have identical or different degrees of crosslinking.

Published U.S. patent application no. US 2007/0196426 A1 discloses a method for producing a biocompatible crosslinked gel consisting in crosslinking a determined quantity of at least one type of liquid biocompatible polymer by adding a quantity of crosslinking agent, in carrying out a crosslinking reaction, in adding an additional quantity of liquid polymer whose molecular mass is greater than 500,000 Da, in solving the reaction mixture in such a way that the total concentration of the liquid polymer is reduced, in crosslinking and in stopping the crosslinking reaction by removing the crosslinking agent.

In published International patent application no. WO 2010/131175 A the process for preparing a crosslinked gel of at least one polymer or one of its salts is disclosed, the process comprising at least the steps that consist in: a) providing an aqueous medium containing at least one polymer, b) forming a homogeneous gel from the medium from step a), c) bringing the gel obtained in step b) into contact with an effective amount of at least one crosslinking agent; d) crosslinking said mixture formed in step c); and e) recovering said crosslinked hydrogel, wherein at least said steps a) to d) are carried out within a hermetic cavity delimited at least partially by a deformable wall, the mixture present in the cavity being exposed, in step d), to conditions conducive to crosslinking.

Finally, published International patent application WO 2011/148116 A relates to a modified hyaluronic acid and to a method for manufacturing said polymer. The modified hyaluronic acid according to this document is a hyaluronic acid modified by grafting at least one amino acid onto same. The document also relates to hyaluronic acid modified for use in treating arthrosis, cancer, urinary incontinence, and as a drug suitable for use in eye surgery or for improving the cicatrization of wounds. The document also relates to the use of a modified hyaluronic acid according to the description as a cosmetic and/or aesthetic product. In all the cosmetic and/or dermatological uses known to those skilled in the art in which HA is used, the HA of the prior art can advantageously be replaced with the modified hyaluronic acid according to the invention. For example, the document relates to the use of the modified HA according to the description as a filling material and/or for increasing a body volume. Examples of said use include, for example, using the modified HA according to this description as a wrinkle-filling material. Another example consists of using the modified HA to increase the volume of the breast or the buttock.

SUMMARY OF THE INVENTION

It is thus an object of the invention to provide a method for crosslinking of hyaluronic acid with the natural amino acid, L-lysine and to have a final product that is completely biosimilar (based on biological building blocks) and biocompatible.

The present invention provides a compound comprising a moiety according to formula (I)

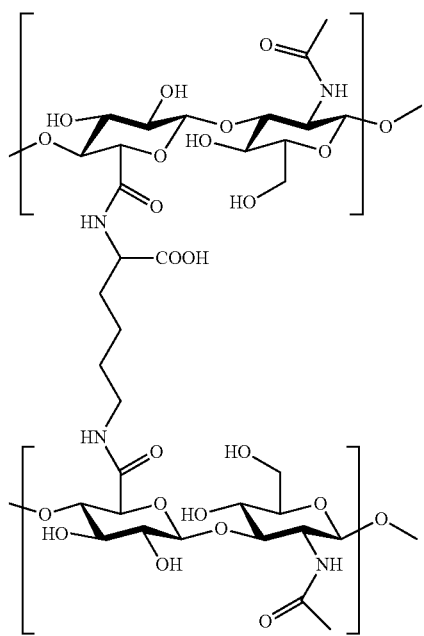

(I)

for use as a medicament.

In a further aspect of the invention, the medicament is a bionic hydrogel that can be used in the treatment of skin and joints, comprising dermal regeneration, restoration and rejuvenation, wherein the treatments of joints may refer to the use of the medicament as a viscosupplement to alleviate pain and improve joint mobility.

It is further intended to use the medicament or bionic hydrogel as a medical solution for wound healing and/or the treatment of scars.

Another object of the present invention relates to a method for the manufacture of a hydrogel, wherein the method is performed in a single step by mixing L-lysine and hyaluronic acid sodium salt in an aqueous solution with EDC and NHS as coupling agents, wherein the single step is performed at a pH in a range between 6 to 7.4

The reaction mixture is left to rest for a time between 1 and 72 hours, or between 4 hours and 24 hours.

In a further aspect of the invented method, the molar ratio between hyaluronic acid sodium salt and L-lysine shall be in the range between 1:0.05 and 1:10, or between 1:0.2 and 1:1.

A further embodiment of the method provides that the single step is performed in a temperature range between 20° C. to 40° C.

The reaction mixture may be cooled to room temperature after finalizing the reaction.

It is also within the scope of the invention that the reaction mixture is dynamically dialyzed against distilled water or PBS using a membrane, wherein PBS is constantly exchanged by circulation against fresh PBS.

In another aspect of the method according to the invention, the resulting hydrogel can be enriched in a subsequent step with physiological salts and/or amino acids in an amount of less than 0.5%-w/w.

Another object of the present invention refers to a method for treating wound healing, intraarticular injections, nerve regeneration, dental care and stomatology, and/or to boost and support regeneration and repair of any damaged tissues or to recover any impaired function, comprising administering to a subject in need thereof a therapeutic effective amount of a compound as described above or a salt thereof.

The formulation can be injected in or implanted into tissues and/or used in topical applications.

BRIEF DESCRIPTION OF THE FIGURES

The invention will be described based on figures. It will be understood that the embodiments and aspects of the invention described in the figures are only examples and do not limit the protective scope of the claims in any way. The invention is defined by the claims and their equivalents. It will be understood that features of one aspect or embodiment of the invention can be combined with a feature of a different aspect or aspects of other embodiments of the invention, in which:

DETAILED DESCRIPTION OF THE INVENTION

Figure 1A:
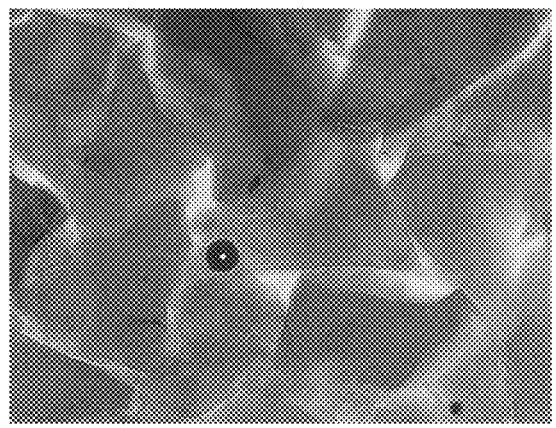
FIGS. 1A and 1B show microscopic pictures of a commercial HA dermal filler crosslinked with BDDE (left) and of the hydrogel according to the present invention (right). The images were obtained by staining the HA with Toluidine Blue for better visualization. It is possible to observe how the material of this invention has a homogeneous, porous structure composed of an isotropic network, in contrast to the particulated texture of the commercially available HA dermal filler.

The invention focuses on several medical applications of hyaluronic acid that is crosslinked to lysine, such as dermal restoration, osteoarthritis, wound healing, scar treatment and regenerative medicine.

The present invention provides a different lysine-based crosslinking strategy, in order to avoid the use of highly toxic molecules such as BDDE. The rationale behind the present invention is to activate the hyaluronan to promote the coupling with L-lysine, following different strategies based on chemical modification of hyaluronic acid and/or activation of the —COOH groups.

The activation of the —COOH group is performed using with non-toxic reagents instead of BDDE.

Regarding dermal restoration, the extracellular matrix (ECM) of dermis is rich in polysaccharides, protein fibers and polyglycopeptides. The entanglement of these biopolymers gives rise to a tridimensional framework where cells navigate and the physiological processes between the cells and outside medium take place. L-Lysine plays an important role in the crosslinking of the collagen fibers, one of the main components of the ECM.

The extracellular matrix of the skin starts to lose volume and viscoelasticity from age 30 onwards. This means that the biopolymers of the biomatrix scaffold will be subjected to cleavage by biodegradation as a part of a natural aging process. On the other hand, the cells turnover of such biopolymers (e.g. polysaccharides, protein fibers and glycoproteins) decrease with age, and so does the tissue repair ability.

The present invention is directed to the novel medical use of an innovative bionic hydrogel—based on the polysaccharide hyaluronic acid and the amino acid lysine—that is intended to restore volume of soft dermal soft tissue, to promote healing of wounds and in scar management. The invented hydrogel possess a unique, homogeneous, isotropic three-dimensional structure that resemble the ECM.

The formulation may be enriched with bioactive ingredients which are known to be of benefit in the extracellular environment.

These include inorganic salts or bio-complexes thereof (e.g. Calcium, Copper, Silver, Zinc but not limited).
  a. These include amino acids, small polypeptides or specific growth factors (e.g. glycine, proline, lysine, histidine, leucine, cysteine, dilysine but not limited to)
  b. These include molecules with antioxidant activity (e.g. vitamins or derivatives of e.g. mannitol . . . )

Osteoarthritis (OA), a degenerative joint disease or degenerative arthritis, is the most common chronic condition of the joints, affecting approximately 200 million people worldwide. OA can affect any joint, but it occurs more often in knees, hips, lower back and neck, small joints of the fingers and the bases of the thumb and big toe.

In normal joints, a firm, rubbery material called cartilage covers the end of each bone. Cartilage provides a smooth, gliding surface for joint motion and acts as a cushion between the bones. In OA, the cartilage breaks down, causing pain, swelling and problems moving the joint. Improving of mobility and relief of pain arthritic joints can temporarily be achieved with the intra articular injection of viscosupplement gel, whose main role is to lubricate the joint.

Viscosupplementation is a procedure for patients suffering of osteoarthritis in which a soft hydrogel is injected into a joint, such as the knee or the elbow, to relieve the pain caused by the lack of synovial fluid or the damage to the cartilage.

To fulfil the lubricating function, the injected gel should show an optimal rheologic profile i.e. viscoelasticity and coating ability. The novel bionic hydrogel has an outstanding rheological profile for elasticity, cohesivity and stretchability, and its mechanical properties can be tuned according to the intended application. The bionic hydrogel may be enriched with bioactive ingredients such as inorganic salts and antioxidants.

Regarding wound healing and the treatment of scars, the formulation has been designed to support the different phases of wound healing, and simultaneously to support wound closure and scar formation. Injury, trauma and surgery leave a cut behind that can be superficial (epidermis, dermis), deep into subcutis or even down to muscle tissue. Every skin cut leads inevitably to the formation of a scar. The aesthetic outcome of a scar is randomly dependent on series of variables, which include but are not limited to e.g. age, health condition, immune system and surgeon hand skills. Today's scar management medical solutions are intended to be used after wound closure. These include topical medical solutions based on silicone gels and laser treatment, just to mention some options.

The basis formulation includes a carbohydrate and an amino acid, L-lysine. Based on morphological (structural) and/or physiological role in the wound healing process, selective biological active ingredients (small biomolecules) have been selected according to their role in boosting and promoting wound healing:
  a. These include inorganic salts or bio-complexes thereof (e.g. Calcium, Copper, Silver, Zinc but not limited).
  b. These include amino acids or small polypeptides or specific growth factors (e.g. glycine, proline, lysine, histidine, leucine, cysteine, but not limited to)
  c. These include molecules with antioxidant activity (e.g. vitamins or derivatives of e.g. mannitol . . . )

Further, the formulation blend may be enriched with anti-bacteriostatic agents (e.g. zinc) to prevent infection during wound healing process.

In order to keep inflammation under control, the formulation blend may be enriched with an anti-inflammatory substance that can be biomolecules, inorganic salts or complexes thereof or a substance from a drug class (e.g. diclofenac)

The formulation is intended to be applied on open wound before closure. The formulation blend must be delivered sterile. Thereafter, during the wound healing process a blend variant may be applied topically for wound care. The topical formulation may be a gel, a hydrogel and/or a dressing impregnated with the blend.

The extracellular matrix (ECM) of the dermis is rich in polysaccharides, protein fibers and poly glycopeptides. The entanglement of these biopolymers give rise to a tridimensional framework where cells navigate and the physiological processes between the cells and outside medium take place. The 3-D-biopolymeric matrix (EM) is renewed and repaired in case of injury, trauma or surgery by cells (e.g. fibroblasts, keratinocytes). Experimental in vitro research has shown that some of the biopolymers (e.g. mucopolysaccharides) or fractions thereof play signal function key roles in signal in tissue repair. Similar signal function interaction with cell membranes towards biological activation has been proved for small biomolecules (e.g. inorganic salts, amino acids and antioxidants).

This invention offers a medical solution to promote and boost wound healing and simultaneously to have a positive bio-effect on scar formation. The exogenous application of a blend of biopolymer(s) and bioactive small moieties on an injury or surgical cut supports the healing process and enhances bio-regeneration. The bioregenerative medical solution gel is intended to be applied in the epidermis down to the surface of subcutis.

The novel formulations have been designed taking into account the different phases of the wound healing process (inflammation, cell proliferation and matrix remodeling), the key biochemical players as well as the endogenous turnover of extracellular matrix components in tissue repairing. The innovative blends have been engineered to be bionic regenerative medical solutions intended to promote and boost regeneration of injured skin tissue. The components of each blend are restricted and limited to their bioactive role of promotion, support and stimulation of dermal tissue repair. Each composition has been leveraged to the site of application in case of surgical cuts. Each composition may be tailored to address variables such aging patients or with impaired wound healing (e.g. diabetics).

Experiments

In order to prolong the resorption time in-vivo, hyaluronic acid has to be stabilised through covalent crosslinking. The degree of crosslinking and, ultimately, the physico-chemical properties and the purity of the synthesized hydrogel are of primary importance for its biocompatibility in the human body. As per today state of the art, all available hyaluronic acid hydrogel medical solutions in the market have been crosslinked by using bridging molecules that are foreigner to the human body. Furthermore, the common crosslinkers used to build hydrogels out of hyaluronic acid have an intrinsic toxicity.

Driven by bionic design, it has been searched for a bio-crosslinker for hyaluronic acid, i.e. a building block present in the human body. Such a hyaluronic acid bio-hydrogel, composed exclusively of biological building blocks, is an optimal regenerative medical solution for rejuvenation, restoration of soft tissue volume and to boost healing. The evaluation of chemical routes for bridging hyaluronic acid chains with a bio-crosslinker lead us to the amino acid L-lysine, which is a feasible bridge to prepare a stabilised hyaluronic acid bio-hydrogel as shown below:

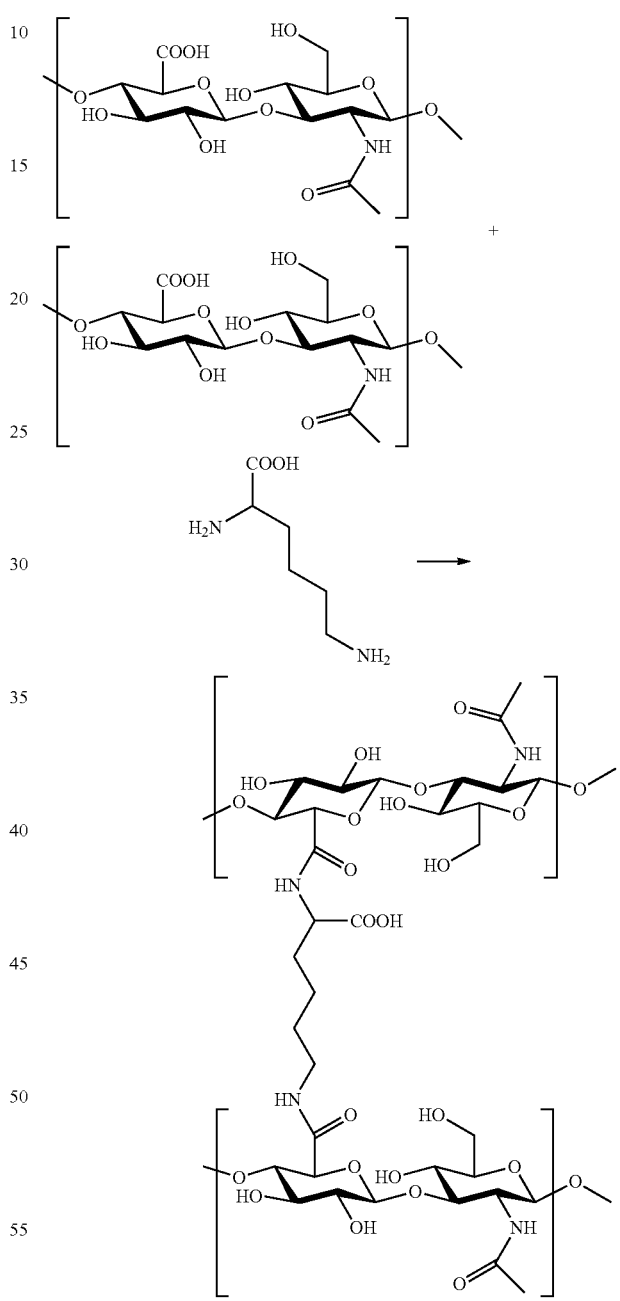

The crosslinking strategy includes the activation of the carboxylic group of the glucuronic acid unit of hyaluronic acid to promote the reaction with the amino groups of the L-lysine crosslinker to form an amide bond. This reaction is well known in literature, especially for it its use in peptide synthesis and in protein labelling, with different reagents and strategy available depending on the specific need.

One promising approach is the use of 1-ethyl-3-(-3-dimethylaminopropyl) carbodiimide hydrochloride (EDC) as an activating agent for the carboxylic group, together with N-hydroxysuccinimmide (NHS), N-hydroxysulfosuccinimide (sulfo-NHS) or 1-hydroxybenzotriazole (HOBt) to further facilitate the reaction, as shown in the following scheme showing the reaction mechanism for coupling an amine to a carboxylic acid moiety through EDC/HOBt:

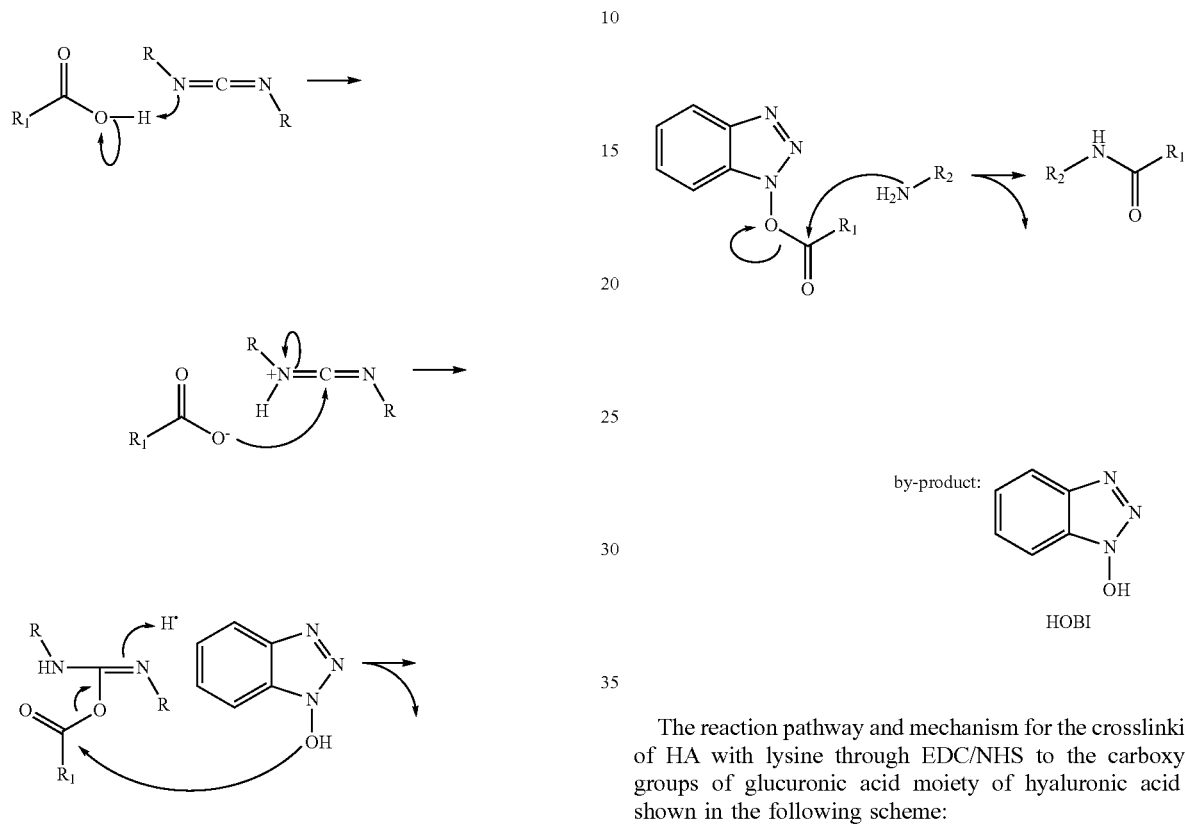

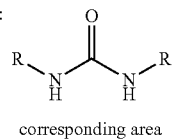

The reaction pathway and mechanism for the crosslinking of HA with lysine through EDC/NHS to the carboxylic groups of glucuronic acid moiety of hyaluronic acid is shown in the following scheme:

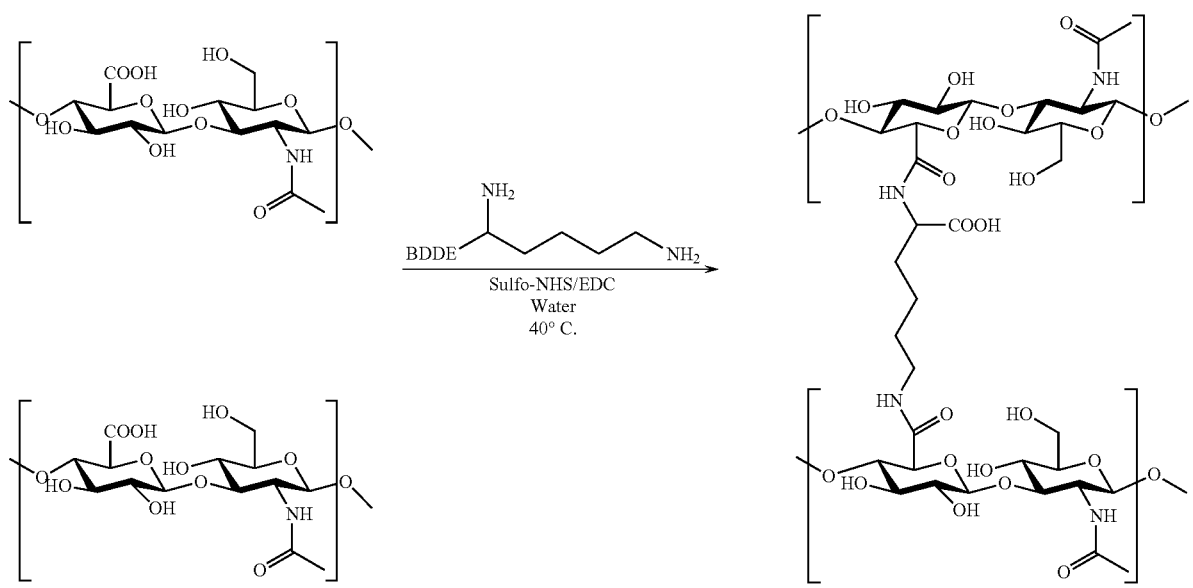

-continued

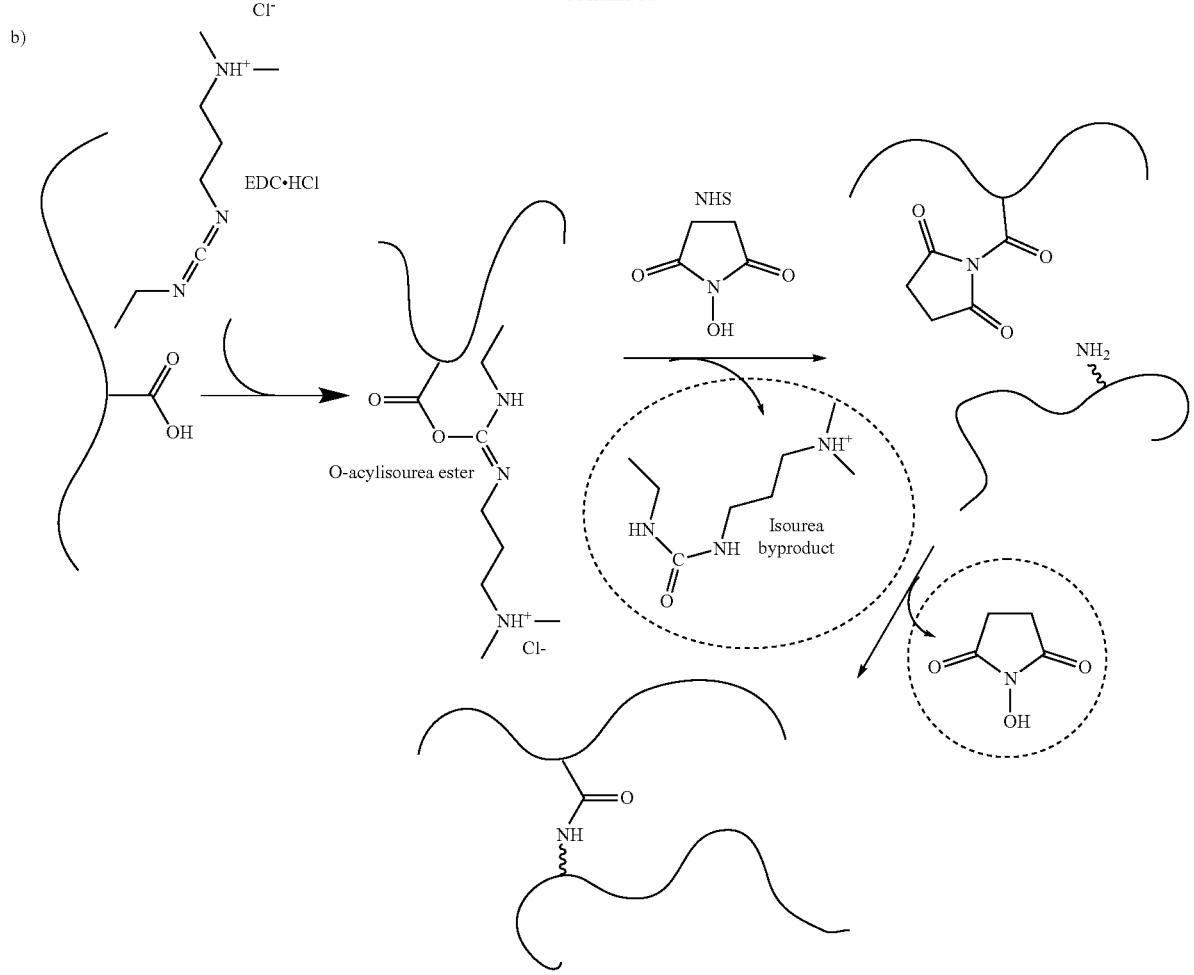

The first step of the reaction is the formation of an O-acylisourea ester of EDC with the carboxylic group of hyaluronic acid. The ester obtained is not stable in water, but it can react with sulfo-NHS to form a more stable intermediate. The activated ester can thus react with an amino group from free L-lysine or from a L-lysine already linked to another chain of the polysaccharide.

The byproducts of the coupling reaction of HA-carboxylic groups-Lysine are water soluble, thus they can be easily removed after the reaction by dynamic dialysis. Dynamic dialysis refers to dialysis where the buffer is constantly exchanged or recirculated. The rheology of the obtained bio-hydrogels can be tuned through pH and molar ratios. The pH can be adjusted and/or tuned with physiological buffers (e.g. PBS, phosphate buffered saline).

To optimize the crosslinking degree of the final product, several parameters must be tuned, such as temperature, adding order of the reagents, concentration, reaction time and pH during the hydrogel preparation. The last parameter is of the utmost importance for several reasons:

The EDC/NHS activation of the —COOH group work better at pH between 5 and 6. Basic pH greatly reduce the yield of the reaction by accelerating the hydrolysis of the intermediate;

L-lysine coupling efficiency depends on pH, and it is most favorable at slightly basic pH, where the amino groups are unprotonated;

Hyaluronic acid can be degraded during the synthesis or the following sterilization process if the pH is not adequate.

In a typical synthesis, Sodium hyaluronate is weighted and dissolved by mechanical stirring in a PBS solution at pH between 5 and 6. The solution obtained has a HA concentration between 3 and 6%. When the mixture is completely homogenous, a solution of NHS in ultrapure water (10 to 40 mg/mL, 0.2-2 eq) is added, and the mixture is mechanically stirred until homogeneity. After, a solution of EDC dihydrochloride is added (0.5-2 g/mL in water, 0.5-3 eq), the mixture is homogenized and left to rest for 5 minutes to 2 hours. Then, a solution of L-Lysine (2-50%, 0.05-2 eq) in PBS at pH=7.4 is added drop by drop to the HA/NHS/EDC mixture. The gel is left to rest for a time between 1 hour and 48 h, then it is transferred into a dialysis bag and purified through dynamic dialysis against PBS at pH=7.4 to remove the traces of unreacted reagents. The hydrogel is sterilized through autoclaving.

Figure 1B:
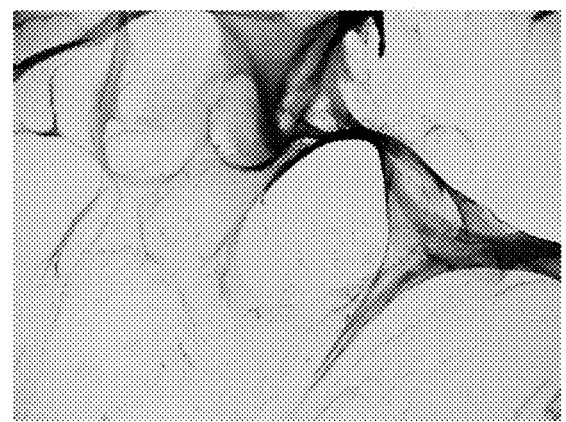

The material obtained is a monophasic, homogeneous hydrogel, with superior rheological properties and a microscopic structure composed of a uniform three-dimensional network. The microscopic structure of the hydrogel is of great importance in the field of regenerative medicine because it allows and enhance cell migration and proliferation. FIG. 1 shows the comparison between a microscopic picture of a standard BDDE-crosslinked hydrogel (left) and the subject of the invention. The images were obtained by staining the HA with Toluidine Blue for better visualization. It is possible to observe how the material of this invention has a homogeneous, porous structure composed of an isotropic network, in contrast to the particulated texture of the commercially available HA dermal filler.

It can be seen in FIG. 1 that standard commercially available hydrogels are in the form of particles dispersed in a non-crosslinked media, while the hydrogel reported of the present invention is a true monophasic and isotropic scaffold. This has a great influence also on the rheological properties of the material, because it gives to the gel extra cohesivity and the ability to sustain stress.

Figure 2:
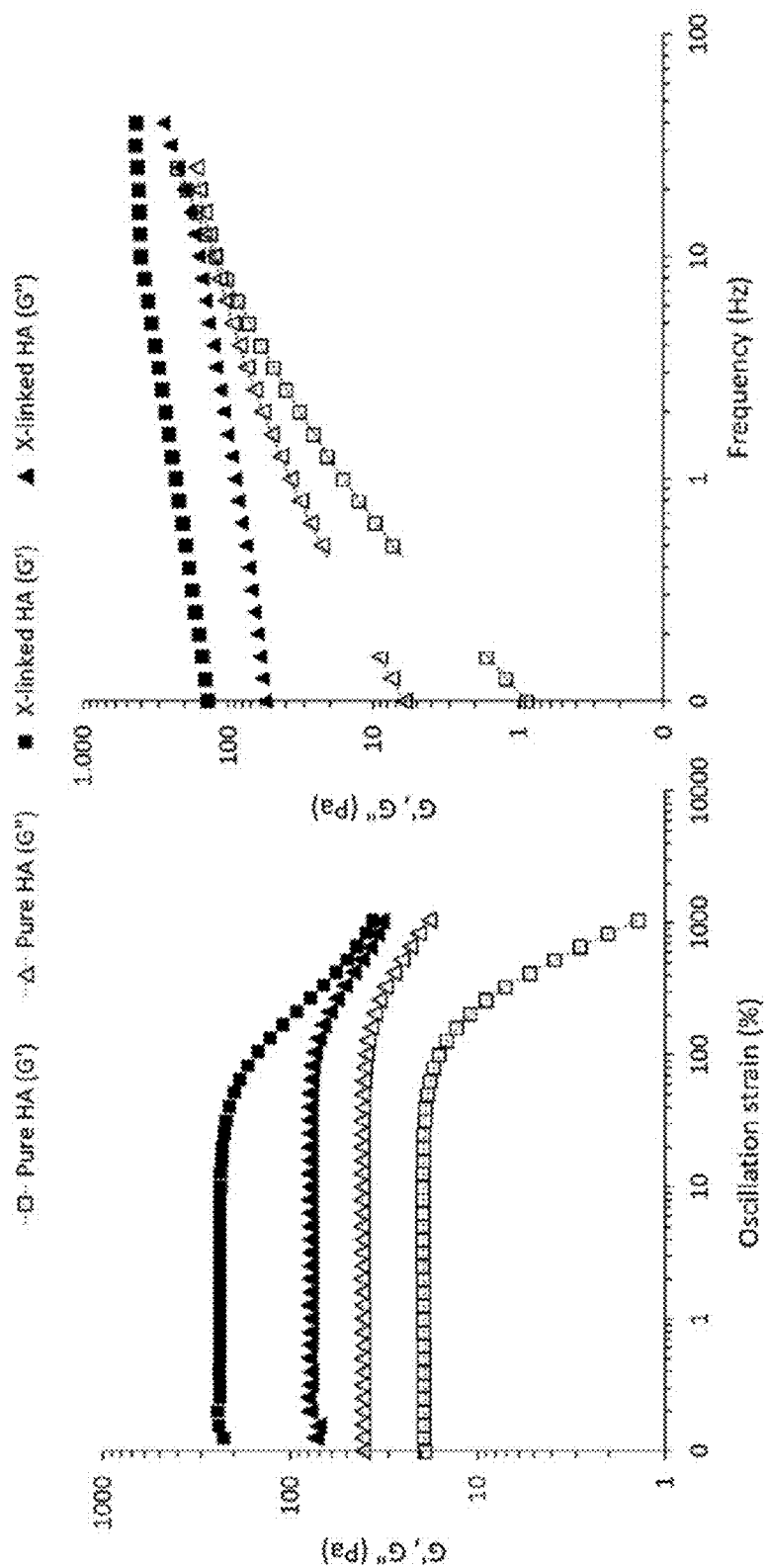
FIG. 2 shows strain sweep at 1 Hz (left) and frequency sweep at 1% strain (right) on pure hyaluronic acid and on lysine-crosslinked hyaluronic acid according to the present invention. Both samples had the same HA concentration, 2.5%. Strain sweep shows that pure HA behaves as a viscous fluid at all strains (G'<G") while crosslinked HA always behaves as an elastic hydrogel (G'>G"). Frequency sweep confirms that lysine-crosslinked HA behaves as a gel in all conditions, while pure HA behaves as a fluid at low frequencies as a gel at higher frequencies.

Oscillatory rheological analysis was performed with a DHR3 rheometer (TA Instruments) equipped with a 35 mm parallel plate geometry, at a constant temperature of 37° C. to simulate the conditions in the human body. FIG. 2 shows the comparison between 25 mg/mL solution of pure hyaluronic acid in PBS buffer at pH=7.4 and 25 mg/mL Lysine-crosslinked hyaluronic acid in strain sweep and frequency sweep experiments. Indeed, it is known that autoclaving as a deep impact on the rheological properties of the material and thus the tests on the invention were performed on the final product, after autoclaving.

It can be taken from the strain sweep at 1 Hz that while pure hyaluronic acid behaves as a viscous fluid (i.e. G'<G") for all the oscillatory strains, the material obtained after the lysine coupling according to the present invention has a solid-like behavior, as expected from a crosslinked hydrogel (G'>G").

Frequency sweep at 1% deformation confirm the same result. While pure hyaluronic acid behaves as a fluid at low frequencies and as a gel at higher frequencies (crossover point at 11 Hz), the crosslinked hydrogel upholds the same gel-like characteristics at all the frequencies.

The rheological properties of the hydrogel can be tuned depending on the ultimate medical use by varying parameters such as HA concentration and HA/EDC/NHS/Lysine molar ratio. For example, the following table 1 report the values of the storage modulus and of the loss modulus for samples prepared in different conditions:

TABLE 1

Values of the storage modulus and of the loss modulus for samples prepared in different conditions.

| | HA concentration | HA/NHS/EDC•HCl/LYS | G' | G" |
|---|---|---|---|---|
| Sample 1 | 30 mg/mL | 1-0.8-0.8-0.5 | 425 | 102 |
| Sample 2 | 25 mg/mL | 1-0.8-0.8-0.8 | 247 | 82 |
| Sample 3 | 20 mg/mL | 1-0.5-0.8-0.8 | 110 | 55 |
| Sample 4 | 20 mg/mL | 1-0.5-0.8-0.4 | 69 | 41 |

With the approach of our invention, materials with the same final concentration of HA can have very different rheological properties depending on the reaction conditions, such as the initial HA concentration or the molar ratio between the reactants. This allows for a precise control of the rheological properties, because it is possible to tune not only the storage and loss modulus, but also other parameters such as cohesivity or elasticity. The control and tuning of the mechanical and rheological properties are crucial in medical applications.

Indeed, one of the most relevant characteristics of the hydrogels obtained with the described process is their cohesivity, elasticity and the ability to sustain stress cycles without breaking in particles. To assess these parameters, we have chosen two different protocols, one to evaluate the elasticity and the stretchability of the invention and one to evaluate its ability to sustain stress cycle without permanent damages.

To evaluate cohesivity and stretchability, extensional measures were carried on a Caber Rheometer (Thermo Fischer) with 4 mm steel pads. The tests were performed over a distance of 10 mm in 9 s and the evolution of the normalized sample diameter with time was recorded. Elasticity was calculated by interpolating the experimental data using the following mathematical model:

$$\frac{D(t)}{D_0} = \left(\frac{GD_0}{4\gamma}\right)^{1/3} e^{\frac{t}{3\lambda_c}}$$

Where $D_0$ is the initial diameter of the filament (in meters); G the elastic modulus of the sample (in Pascal) and $\lambda_c$ the relaxation time (in seconds).

Figure 3:
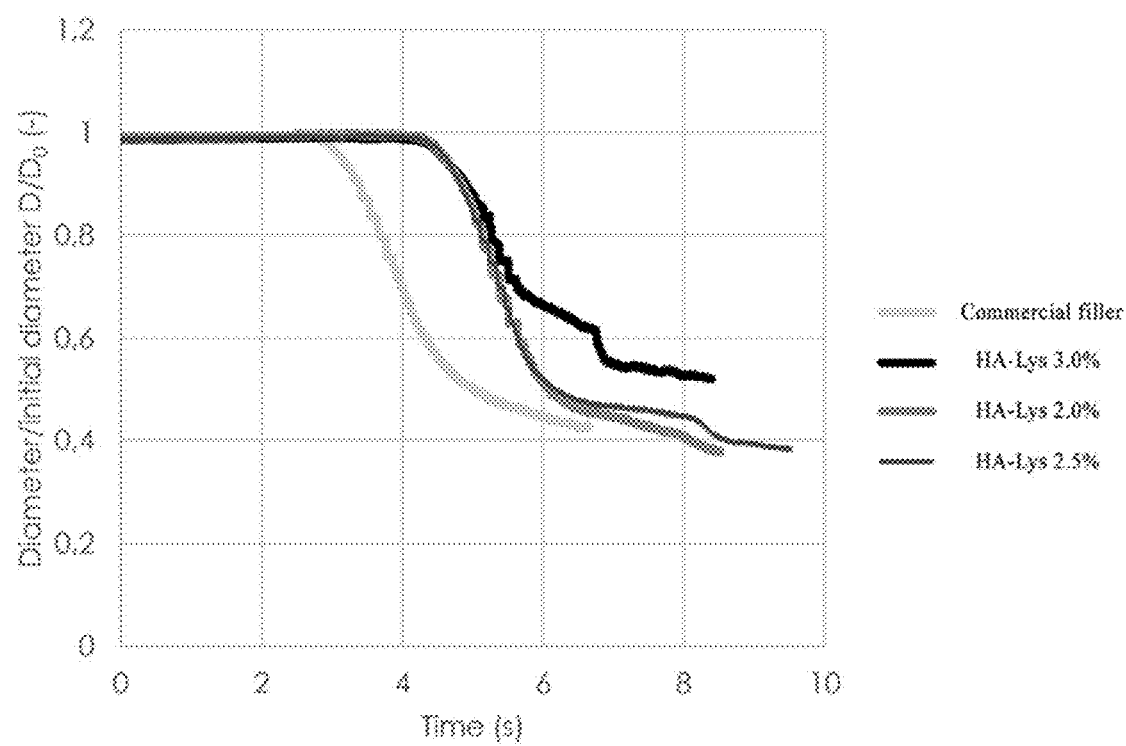
FIG. 3 shows extensional measures to determine the elasticity and cohesivity of HA-Lys hydrogels (30, 25 and 20 mg/mL respectively) in comparison with a standard BDDE-crosslinked dermal filler (28 mg/mL HA). This test simulates the "finger test" usually performed by the expert in this sector to judge the cohesivity of the hydrogel. It is possible to observe how the diameter of the commercial dermal filler decades much faster in comparison the corresponding HA-Lys hydrogels, showing how the hydrogels reported in this invention have a significantly better cohesivity and thus will give to future patients a softer feeling and a more natural look.

FIG. 3 shows the result of the extensional measure on a standard, monophasic, a commercial 28 mg/mL, monophasic, BDDE-crosslinked hydrogel in comparison with three different hydrogels crosslinked with L-lysine according to the method of the present invention.

This test simulates the "finger test" usually performed by the skilled artisan in this sector to judge the cohesivity of the hydrogel. It is possible to observe how the diameter of the commercial dermal filler decades much faster in comparison the corresponding HA-Lys hydrogels, showing how the hydrogels reported in this invention have a significantly better cohesivity and thus will give to future patients a softer feeling and a more natural look The results of the experiments in FIG. 3 show that the lysine-crosslinked hydrogel of the present invention becomes thinner slower in comparison to a standard monophasic hydrogel, confirming the higher cohesivity of the materials obtained with the new process. This can be linked to the special microscopic structure composed of a homogeneous three-dimensional network.

The elastic modulus (G, reported in Table 2 for a range of HA concentration between 20 and 30 mg/mL) is generally lower compared to commercial HA-BDDE hydrogel. This confirms that the HA-LYS hydrogels are more cohesive but also that they can be elongated with lower force compared to standard HA-BDDE gels. This is vital for safety and efficacy in medical applications, because it means that HA-Lys hydrogels adapt better to surrounding tissues and no not break under stress. From a clinical point of view, this also means, that the present invention, in comparison to commercially available dermal fillers, potentially modulate better to the tissue and the patient doesn't feel the hydrogel. This is relevant, for instance, when the invention is employed in anatomical area where it has to bear mechanical loads, such as in dermal and intra-articular injections. From this elongation study it is possible to conclude that the crosslinking of HA with L-Lysine following the reported method allows the preparation of hydrogels that can be stretched by application of a lower force in comparison to standard BDDE hydrogel, while maintaining its cohesivity.

TABLE 2

Comparison of samples with different HA concentrations

|  | HA concentration | HA/NHS/EDC•HCl/LYS | Elasticity (G, kPa) |
|---|---|---|---|
| Sample 1 | 30 mg/mL | 1-0.8-0.8-0.5 | 24 |
| Sample 2 | 25 mg/mL | 1-0.8-0.8-0.8 | 58 |
| Sample 3 | 20 mg/mL | 1-0.5-0.8-0.8 | 6 |
| Commercial dermal filler | 28 mg/mL | BDDE crosslinked | 148 |

In another experiment, the material underwent several cycles of compression to evaluate the resistance to chronic stress. The experiments were performed on a DHR3 rheometer (TA Instruments) equipped with rough 25 mm parallel plate geometry. For these tests, the gap is set to 1 mm. A frequency sweep from 0.5 to 5 Hz at 0.1% strain is performed. The gap is then set to 0.9 mm at 5 μm/s. another frequency test is performed. The gap is then set to 1 mm again at the same speed. Another frequency test is performed. The cycle is then repeated 10 times in total. Each frequency test interrogates the structure of the gel and its capacity to absorb or to dissipate energy.

Figure 4:
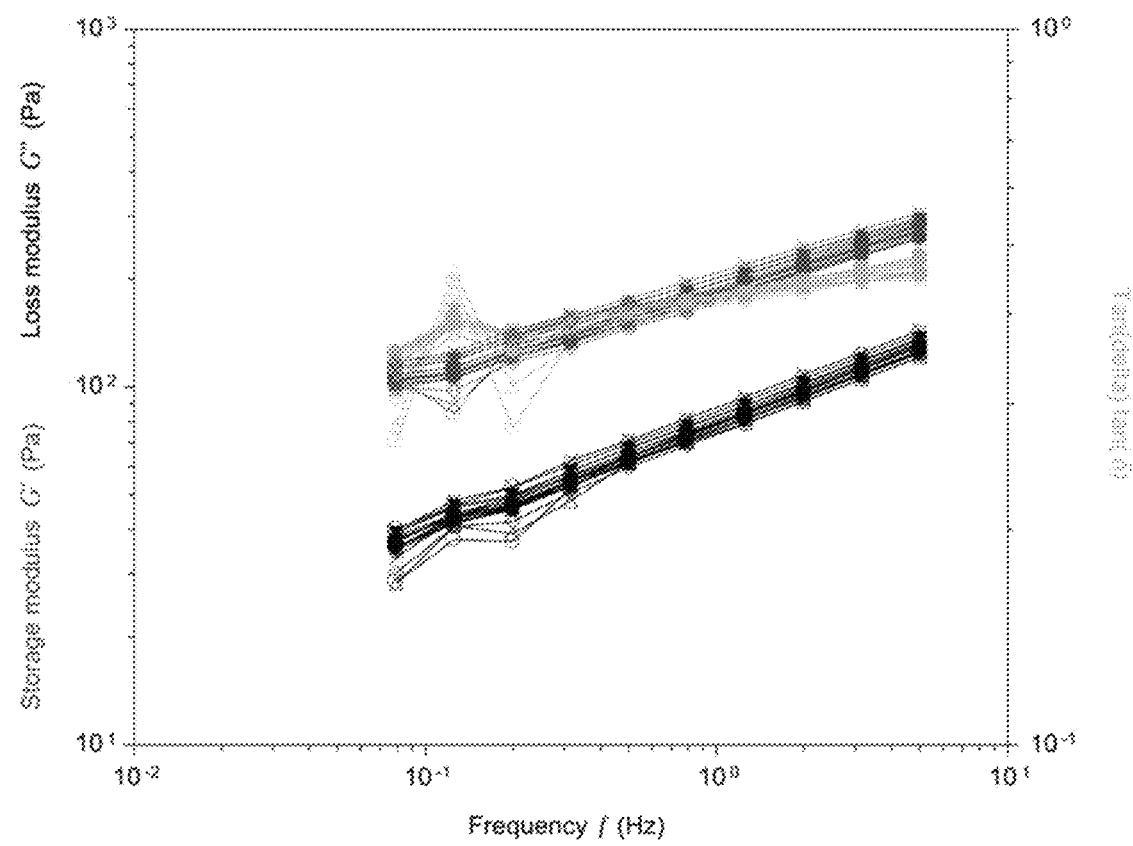
FIG. 4 shows repeated cycles of compression at different frequencies on a L-Lysine cross-linked HA hydrogel with a 3.0% concentration. The test show how the invention is able to quickly absorb repeated stress even at very high frequencies without any internal damage to the microscopic structure. This especially relevant in applications in dermal restoration or intra-articular injections.

FIG. 4 shows the results of such experiments, in which repeated cycles of compression at different frequencies were performed on a L-Lysine cross-linked HA hydrogel with 3.0% concentration. It can be taken from FIG. 4 that the HA-Lysine hydrogels are able to sustain compression-elongation cycles at different frequencies without any significant change in their response, and thus no damage to their inner structure. Even at higher frequencies, the difference in the loss and storage modulus are negligible between each cycle. This behavior is of the utmost importance for medical applications such as dermal restoration and intraarticular injections.

HA is naturally degraded in the body due to the action of free radicals and, more importantly, by a specific class of enzymes called hyaluronidases. These enzymes are commercially available and are already employed in aesthetic medicine to trigger the degradation of HA-based dermal filler when it is necessary to dissolve it in order avoid complications or to correct injection errors.

The measure of the degradation rate of HA hydrogels with hyaluronidases is the most reliable method to simulate the in-vivo conditions of the human body. The experiments were conducted using a 6080 U/ml Type I-S hyaluronidase from bovine testes. For each sample, 0.2 g of hydrogel were centrifuged, and the enzyme solution was then added. At each time point (1 h, 3 h, 6 h, 24 h, 48 h, 72 h, 120 h and 168 h) the enzymatic reaction was interrupted adding a solution of potassium tetraborate solution, followed by a stirring with a vortex mixer and heating at 100° C. The tubes were then cooled at room temperature and the amount of N-acetylglucosamine released was measured.

The following parameters were evaluated:

$Deg_{max}$=maximum percentage of degradation observed in the described conditions $T_{1/2}$=time in hours required to reach 50% of $Deg_{max}$ $T_{50}$=time in hours required to reach 50% of the total HA degraded.

In Table 3 are reported the results of the degradation study on one commercially available BDDE-crosslinked HA hydrogel and on two samples of HA crosslinked with L-Lysine according to our new technology.

TABLE 3

Degradation study

|  | HA concentration | HA/NHS/EDC•HCl/LYS | $Deg_{max}$ | $T_{1/2}$ | $T_{50}$ |
|---|---|---|---|---|---|
| Sample 1 | 30 mg/mL | 1-0.8-0.8-0.5 | 95.28 ± 8.68 | 58.26 ± 3.21 | 64.33 |
| Sample 3 | 20 mg/mL | 1-0.5-0.8-0.8 | 80.26 ± 2.00 | 35.26 ± 2.30 | 47.20 |
| Commercial Dermal Filler | 28 mg/mL | BDDE crosslinked | 83.25 ± 5.32 | 37.71 ± 7.19 | 45.60 |

The data compiled in the above table 3, show that the 30 mg HA/mL Lysine-crosslinked hydrogel has a slower degradation rate in comparison to a standard HA-BDDE crosslinked hydrogel with 28 mg HA/mL, while the 20 mg HA/mL Lysine-crosslinked hydrogel has a comparable degradation kinetic. This confirms that the novel hydrogels are indeed stable over time and have a lower degradation rate in comparison to standard HA-BDDE hydrogels available in the market. From a chemical point of view, this shows that the optimized conditions employed during the synthesis allow the coupling of L-Lysine to HA through the formation of stable amide bonds, instead of the less stable ester bonds obtained with other EDC/NHS coupling protocols reported in literature.

In another experiment, hyaluronic acid sodium salt is dissolved in a 0.9% physiological solution of NaCl. EDC is added to the HA gel solution (molar ratio 1:0.1-1:2), immediately followed by the addition of a solution of N-hydroxysulfosuccinimide sodium salt in 0.9% NaCl. After, a solution of L-Lysine is added and the mixture is kept at 40° C. for one hour. The molar ratio of all reagents is (1 HA:1 EDC:1 NHS: 1.8 Lysine). The final product is purified by dialysis against PBS using a 6-8000 MWCO membrane.

Hyaluronic acid sodium salt is dissolved in of saline solution 0.9%. EDC is added to the HA gel solution (molar ratio 1:0.7) immediately followed by a solution of N-hydroxysulfosuccinimide sodium salt in saline solution. After, a solution of L-Lysine is added and the mixture is kept at 40° C. for one hour. The molar ratio of all reagents is (1 HA:0.5 EDC:0.5 NHS:0.5 Lysine). The final product is purified by dialysis against distilled water 6-8000 MWCO membrane.

After dialysis the bio-hydrogel may be enriched with physiological salts (e.g. Calcium chloride, Zinc chloride) in an amount lower than 0.5%, and/or amino acids (e.g. proline, cysteine, glycine) in an amount lower than 0.5%. The homogenization through diffusion of the salts or amino acids in the hydrogel matrix is performed by shaking for at least 1 hour. Thereafter, the concentration of HA in the bio-hydrogel is tuned to the target concentration with PBS. Finally, the full hydrated and equilibrated bio-hydrogel is sterilized through steam sterilization at 121° C.

It is an advantage of the claimed method for manufacture that it comprises only one step in comparison to a sequence of steps for adding compounds and adjusting parameters. Any side products resulting from the claimed method are non-toxic. Finally, the present invention provides a fast method for manufacturing a biocompatible gel of hyaluronic acid crosslinked by lysine in comparison to methods known from the prior art.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment was chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

What is claimed is:

1. A method for the manufacture of an L-lysine cross-linked hyaluronic acid hydrogel from EDC/NHS activated hyaluronic acid sodium salt, wherein the crosslinking is performed in a single step by mixing L-lysine and hyaluronic acid sodium salt in an aqueous solution with EDC and NHS as coupling agent, wherein the single step is performed at a pH in a range between 6 to 7.4.

2. The method of claim 1, wherein the reaction mixture is left to rest for a time between 1 and 72 hours.

3. The method of claim 1, wherein the reaction mixture is left for a time between 4 to 24 hours to rest.

4. The method of claim 1, wherein the molar ratio between hyaluronic acid sodium salt and L-lysine is in a range between 1:0.05 and 1:10.

5. The method of claim 1, wherein the molar ratio between hyaluronic acid sodium salt and L-lysine is in the range between 1:0.2 and 1:1.

6. The method of claim 1, wherein the single step is performed in a temperature range between 20° C. to 40° C.

7. The method of claim 1, wherein the reaction mixture is kept at 40° C. for one hour and then cooled to room temperature.

8. The method of claim 1, wherein the reaction mixture is dynamically dialyzed against distilled water or phosphate-buffered saline (PBS) using a membrane.

9. The method of claim 8, wherein the PBS is constantly exchanged by circulation against fresh PBS.

10. The method of claim 1, wherein the resulting hydrogel is enriched in a subsequent step with physiological salts and/or amino acids in an amount of less than 0.5%-w/w.

11. The method of claim 1 further comprising adjusting a pH of the aqueous solution mixture containing L-lysine and hyaluronic acid sodium salt to be in a range between 6 to 7.4 by adding PBS to the aqueous solution mixture.

* * * * *